United States Patent
Monty et al.

(10) Patent No.: US 9,980,788 B2
(45) Date of Patent: May 29, 2018

(54) SYSTEMS AND METHODS FOR GROUNDING OR ISOLATING A DENTAL HAND PIECE

(71) Applicant: Convergent Dental, Inc., Natick, MA (US)

(72) Inventors: Nathan P. Monty, Shrewsbury, MA (US); William H. Groves, Jr., Arlington, MA (US)

(73) Assignee: Convergent Dental, Inc., Needham, MA (US)

( * ) Notice: Subject to any disclaimer, the term of this patent is extended or adjusted under 35 U.S.C. 154(b) by 353 days.

(21) Appl. No.: 14/554,482

(22) Filed: Nov. 26, 2014

(65) Prior Publication Data

US 2015/0150648 A1    Jun. 4, 2015

Related U.S. Application Data

(60) Provisional application No. 61/909,926, filed on Nov. 27, 2013.

(51) Int. Cl.
| | |
|---|---|
| *A61C 1/00* | (2006.01) |
| *A61C 3/00* | (2006.01) |
| *A61C 1/06* | (2006.01) |
| *A61B 18/20* | (2006.01) |

(52) U.S. Cl.
CPC .......... *A61C 1/0046* (2013.01); *A61C 1/0015* (2013.01); *A61C 1/06* (2013.01); *A61B 18/201* (2013.01); *Y10T 29/49002* (2015.01)

(58) Field of Classification Search
CPC ... A61B 18/201; A61C 1/0015; A61C 1/0046; A61C 1/06; Y10T 29/49002
See application file for complete search history.

(56) References Cited

U.S. PATENT DOCUMENTS

| | | |
|---|---|---|
| 3,528,424 A | 9/1970 | Ayres |
| 4,697,590 A | 10/1987 | Nakai et al. |
| 5,343,391 A | 8/1994 | Mushabac |

(Continued)

FOREIGN PATENT DOCUMENTS

| | | |
|---|---|---|
| JP | 2009000544 A | 1/2009 |
| WO | WO-2013/160888 A3 | 1/2014 |

OTHER PUBLICATIONS

International Search Report and Written Opinion for International Patent Application No. PCT/US2014/067635 dated Mar. 24, 2015 (10 Pages).

(Continued)

*Primary Examiner* — Lindsey G Wehrheim
(74) *Attorney, Agent, or Firm* — Goodwin Procter LLP

(57) ABSTRACT

An electrically safe treatment system for use in treating a patient includes two or more sections coupled with a joint that permits any one section to rotate relative to another coupled section. At least one of the sections includes an electrical component. An electrical contact associated with the joint is designed to maintain an electrical connection between a pair of sections throughout an angular range of motion of one of the sections relative to the other, coupled section. The electrical contact can also maintain a total resistance of a series connection including the two sections and the contact below a specified threshold. Alternatively, one or more insulator joints may be employed to meet safety requirements.

22 Claims, 2 Drawing Sheets

(56) References Cited

U.S. PATENT DOCUMENTS

| | | |
|---|---|---|
| 5,748,657 A | 5/1998 | Gaddis |
| 6,117,129 A | 9/2000 | Mukai |
| 7,951,139 B2 | 5/2011 | Assa et al. |
| 2003/0028181 A1 | 2/2003 | Enomoto |
| 2003/0165794 A1 | 9/2003 | Matoba |
| 2004/0059197 A1 | 3/2004 | Yamashita et al. |
| 2005/0215987 A1 | 9/2005 | Slatkine |
| 2007/0167943 A1 | 7/2007 | Janssen et al. |
| 2009/0215004 A1* | 8/2009 | Whitman ............... F16M 11/14 433/29 |
| 2009/0230269 A1 | 9/2009 | Dallarosa |
| 2010/0104736 A1 | 4/2010 | Luce et al. |
| 2011/0189628 A1 | 8/2011 | Monty |
| 2014/0170588 A1 | 6/2014 | Miller et al. |
| 2014/0272767 A1 | 9/2014 | Monty |

OTHER PUBLICATIONS

"Principles of Electrical Safety Testing of Medical Equipment", American River College, Intro to Biomed Equipment Technology, Electrical Engineering 426, Jan. 27, 2009.

* cited by examiner

SYSTEMS AND METHODS FOR GROUNDING OR ISOLATING A DENTAL HAND PIECE

CROSS-REFERENCE TO RELATED APPLICATIONS

This application claims benefit of priority to U.S. Provisional Patent Application No. 61/909,926, entitled "Grounded or Isolated Dental Hand Piece," filed on Nov. 27, 2013, the contents of which are incorporated herein by reference in their entirety.

FIELD OF THE INVENTION

The present disclosure generally relates to electrical grounding or isolation and, in particular, to grounding or isolation of a dental laser hand piece for use with a dental laser ablation system.

BACKGROUND

Traditionally different devices are used in the practice of dentistry, e.g., to view, drill, inspect, diagnose, and measure teeth. When one instrument is used and then removed from the person's mouth, the data collected can be saved but the references used in collecting the data (e.g., location of the instrument relative to a person's mouth) may be lost. If different instruments are incorporated into a single dental hand piece, the references can be maintained between functional analysis groups and greater accuracy and better treatment can be achieved. Different instruments, however, require different input powers, voltages, operating currents, etc. which can increase the risk of unwanted or harmful electrical contact between an electrical instrument and/or other treatment apparatus and a person to be treated.

Lasers are known to be useful in several hard and soft tissue dental procedures, including: removing decay, cutting, drilling or shaping hard tissue, and removing or cutting soft tissue. A tooth has three layers. The outermost layer is the enamel which is the hardest and forms a protective layer for the rest of the tooth. The middle and bulk of the tooth is made up of dentin, and the innermost layer is the pulp. The enamel and dentin are similar in composition and are roughly at least 70% mineral by weight, which is generally carbonated hydroxyapatite, while the pulp contains vessels and nerves. Laser radiations at a wavelength between 9.3-9.6 micrometer ($\mu$m) range are well absorbed by the hydroxyapatite that is typically a major component of teeth and bones, making such lasers efficient in the removal of hard tissue. Lasers in the above stated wavelength range and that have sufficient power for use in dental and/or surgical procedures can be manufactured at a low price to allow for commercial use of such lasers.

Lasers are known to be useful in the removal of dental material generally without the need for local anesthetic that is usually required when a similar procedure is performed using a conventional drill or bur. Moreover, lasers generally do not make the noises and vibrations that are associated with dental drills. At least for these reasons, it has been the hope of many in the dental industry that lasers would replace the drill because they may reduce the anxiety and fear generally associated with conventional dental treatment.

Various inspection and diagnostic tools, such as intra-oral cameras, caries fluorescence sensors, and two-dimensional (2D) and three-dimensional (3D) measurement scanners, are commonly used in modern dentistry. All of these instruments are generally placed one at a time in the mouth of a person and data are collected. When a device is removed from the mouth, some or all of the corresponding references and data may be lost. As such, each instrument may need to create its own reference orientation independently of the other devices used during the course of the treatment.

Operators (e.g., dentists, dental clinicians, etc.) may use a rotatable hand piece and bur. The dental hand piece and bur are typically used to remove enamel by mechanical shearing, providing the operator position and tactile feedback while cutting. The width and length of the rotating bur can be used to estimate position and depth of the cut, while pressing on the bur can provide tactile feedback. The rotatable hand piece and bur, however, do not provide any useful reference to other devices such as cameras, scanners, etc., and do not use any reference data from such other devices used in treatment.

SUMMARY OF THE INVENTION

In order to improve treatment quality and efficiency, it is beneficial to provide a common reference and datum plane to different instruments and devices used for treatment. One way to achieve a common reference plane is to house various instruments in a single hand piece, e.g., a dental hand piece, or in a system where various instruments located outside the hand piece can nevertheless collect data from light received through a single hand piece. This may allow the operator to hold/place a single hand piece inside a person's mouth during the treatment, without having to swap in and out several instruments.

For example, enabling image capture by a vision system and laser-beam guidance through a single hand piece may allow an operator to see and drill a tooth without changing devices. If a diagnostic instrument is also added, a tooth can be viewed, diagnosed, and drilled without switching any devices. Further, if a measurement instrument is added, a tooth can be viewed, diagnosed, drilled, and measured without having to switch from one device to another. The commonality of a single hand piece can facilitate passing of the reference planes and data from one treatment/analysis instrument to another in a seamless manner. To this end, different instruments or one or more powered components of one or more of the instruments may be located within the hand piece. U.S. Patent Application Pub. No. 2014/0272767 and U.S. Patent Application Pub. No. 2014/0272775 describe hand pieces and housing/main chambers that contain one or more vision, diagnosis, measurement, and beam-guidance instruments and/or powered components thereof. The entire contents of both publications are incorporated herein by reference in their entireties.

Different instruments typically have different power supply requirements such as different voltages, current, and/or power specifications, AC or DC supply requirements, and/or ratings. Housing one or more instruments and/or powered components thereof in a hand piece, therefore, typically requires electrically grounding and/or isolating the instruments and/or components thereof from each other and/or from the hand piece placed in a person's proximity, e.g., in the mouth, for dental treatment. For safety, generally the hand piece must be ground bonded to the mains power entry-point earth-ground, and the grounding is typically verified by the application of 25 Amps current across the entire system with a limit of less than or equal to 0.1 ohm resistance for equipment with a fixed power cord and less than or equal to 0.2 ohms resistance for equipment with a detachable power cord. Additionally, if the hand piece is detachable, it is desirable to provide a positive lock, e.g., a mechanical lock such as a clamp, between the detachable hand piece section and the grounded section of the instrument, with the detachable hand piece grounded well enough to the grounded section of the instrument, such that the application of 25 Amps current across the entire instrument with a limit of no more than 0.1 ohm for equipment with a fixed power cord and no more than 0.2 ohms for equipment with a detachable power cord is satisfied. A positive lock, however, can interfere with or limit the rotatibility of the hand piece.

In a laser-based dental treatment system, for the rotatable sections of the beam delivery apparatus or a rotatable hand piece section, the bearings generally include clearances and grease, such that electrical connectivity or grounding through the bearings is often not sufficient to satisfy the above described requirements to ensure patient safety. A positive lock can interfere with or prevent the rotatability of the hand piece, which can make targeting a particular region for treatment difficult.

Various instruments or powered components thereof that are mounted in a dental hand piece and that share instrument reference data can allow the operator to treat a patient's tooth quickly and accurately. Such an integrated dental hand piece that is to be placed in a patient's mouth needs to be safely electrically grounded or isolated, however, so that quick and effective treatment is achieved while safety of the person to be treated is maintained. A dental hand piece integrating various instruments and/or components thereof in a safe manner can greatly enhance the advantages and benefits that laser technology can offer modern dentistry. Therefore, various embodiments described herein feature systems and methods that can provide a common low resistance grounding to different instruments used in treatment or, in the alternative, electrical isolation of the different instruments.

In particular, various embodiments of the present invention feature flexible (e.g., resilient and/or compliant), low-resistance electrical contacts that provides electrical continuity between rotatably attached sections of a treatment system. In the alternative, an equipment section can be isolated from one or more other sections using insulators that can withstand a specified voltage potential greater than 500 V.

According to a first aspect, an electrically safe treatment system for use in treating a patient includes a first section including an electrical component, a second section rotatably affixed to the first section via a first joint, and a first electrical contact associated with the first joint. The first contact is adapted to maintain an electrical connection between the first section and the second section throughout an angular range of motion of the second section relative to the first section and also maintain a total resistance of a series connection of the first section, the second section, and the first contact below a specified threshold.

In various embodiments, the first section can include a housing forming a main chamber of a laser beam delivery system and the second section includes a hand piece adapted to guide a laser beam to a treatment area. In one embodiment, the first joint includes a bearing and the first electrical contact includes a resilient metal and/or a coated polymer. In certain embodiments, the system further includes a third section rotatably affixed to the first section via a second joint. An electrical cable provides electrical contact with the first section, the third section, and the ground. The first contact is adapted, e.g., by selecting shape, structure, and/or materials thereof, so as to maintain a total resistance of a series connection defined by the cable, the first section, the second section, and the first contact below the specified threshold.

In some embodiments, the second joint includes an insulator joint. In other embodiments, the second joint includes a second electrical contact, and the first and second electrical contacts are adapted so as to maintain a total resistance of a connection defined by the cable, the first section, the second section, the third section, and the first and second electrical contacts is less than a specified threshold, e.g., 0.2 ohm, 0.1 ohm, 0.05 ohm, 0.02 ohm, etc.

In various embodiments, the electrical component can be any one or more of a servo motor, an intra-oral camera, a caries fluorescence sensor, a two-dimensional measurement scanner, and a three-dimensional measurement scanner. In some embodiments, the second section may include one or more of an intra-oral camera, a caries fluorescence sensor, a two-dimensional measurement scanner, and a three-dimensional measurement scanner. The first joint may be a knuckle joint or any other joint having one or more degrees of freedom. In some embodiments, the first contact can include a flexible, conductive elongate element. In certain embodiments, the specified threshold is about 0.1 ohm.

According to another aspect, an electrically safe treatment system for use in treating a patient includes a first section including a first electrical component, a second section rotatably affixed to the first section, and a third section rotatably affixed to the first section via an insulator joint. In certain of these embodiments, the third section may be made of a substantially electrically non-conductive material, for example a carbon fiber material. In some embodiments, the third section can include a second electrical component and the insulator joint is adapted to provide electrical isolation between the first electrical component and the second electrical component at least at a potential voltage at a specified value, e.g., 1000 V, 2000 V, 10 KV, etc.

Various electrical components can be used, including one or more of a servo motor, an intra-oral camera, a caries fluorescence sensor, a two-dimensional measurement scanner, and a three-dimensional measurement scanner. In certain embodiments, the high potential value is at least about 2000 volts. The insulator joint may be a knuckle joint or any other joint having one or more degrees of freedom.

In one particular embodiment, the third section may include an articulating arm, the second electrical component may be a laser generator, the first section may include a housing forming a main chamber of a laser beam delivery system, and the second section may include a hand piece adapted to guide a laser beam to a treatment area. The laser generator is or includes a radio-frequency (RF) excited $CO_2$ laser filled with gas at a pressure in a range of about 260 to 600 Torr.

According to yet another aspect of the invention, a method of maintaining an electrically safe treatment system for use in treating a patient includes providing a treatment system including a first section including an electrical component, a second section rotatably affixed to the first section via a joint, and an electrical contact associated with the joint. The method further includes maintaining an electrical connection between the first section and the second section throughout an angular range of motion of the second section relative to the first section and maintaining a total resistance of a series connection between the first section, the second section, and the contact below a specified threshold.

According to still another aspect of the invention, a method of maintaining an electrically safe treatment system for use in treating a patient includes providing a treatment system including a first section including a first electrical component, a second section rotatably affixed to the first section, and a third section rotatably affixed to the first section, and providing an insulator joint between the first section and the third section.

BRIEF DESCRIPTION OF THE DRAWINGS

Various aspects and features of the present the invention will be more fully understood with reference to the following detailed description in conjunction with the drawings of which.

DETAILED DESCRIPTION

Figure 1:
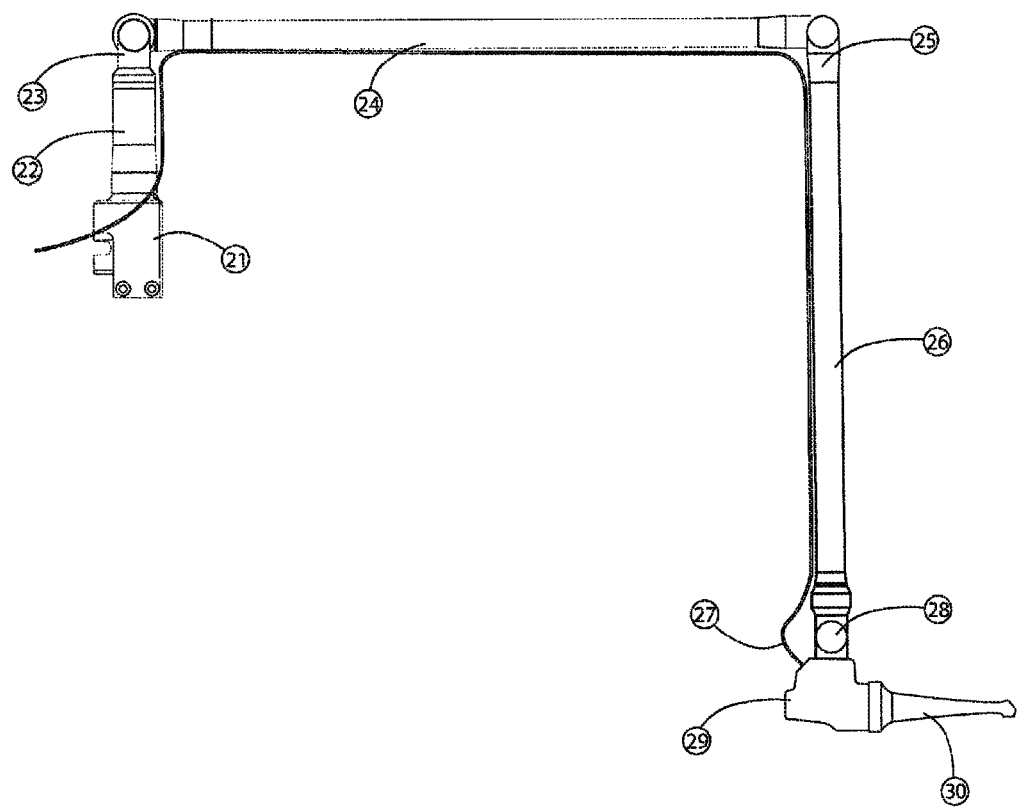
FIG. 1 is a schematic representation of a conductive wire series connection for grounding a dental hand piece at a distal end of a laser beam delivery system in accordance with one embodiment of the invention.

With reference to FIG. 1, a laser-beam-delivery system 100 includes a laser-beam-generation system 21, such as that described in U.S. Patent Application Publication No. 2013/0059264 entitled Laser Based Computer Controlled Dental Preparation System, which is hereby incorporated herein by reference in its entirety. In order to deliver the laser beam to a treatment area, the system 100 includes a number of tubular elements forming clear apertures 22, 24, 26 connected via swiveling knuckles 23, 25, 28. The apertures can transmit a laser beam therethrough while maintaining alignment. A dental hand piece 30 is attached to an instrument housing/main chamber section 29. Various devices can be located within the laser-beam generation system 21, the housing/main chamber section 29, and/or the hand piece 30. To generate efficiently laser radiation at wavelengths approximately in the 9.3-9.6 µm range, in the form of pulses having widths in a range from about 1 µs up to about 30 µs, or up to about 100 µs, or up to about 250 µs, or even up to about 500 µs, the laser-beam generation system 21 may include a radio frequency (RF) excited $CO_2$ laser operated using gas at a pressure in a range of about 260 Torr to about 600 Torr. Such a laser is described in U.S. Patent Application Pub. No. 2011-0189628A1, the contents of which are incorporated herein by reference in their entirety.

A grounding wire 27 is routed along various sections of the beam-delivery system 100 to ensure that all instruments located in those sections, such as the beam-generation system 21, the housing/main chamber 29, etc., are electrically grounded adequately. Such a wire, however, can make the construction and/or operation of the beam-delivery system cumbersome. If the hand piece 30 is also grounded as described below it is generally safe to use the hand piece 30 in a person's mouth.

The dental hand piece 30 can be removably and rotatably attached to the housing/main chamber section 29. The grounding wire is often not routed to the hand piece 30 so as not to interfere with rotatability of the hand piece 30. So as not to interfere with the bearings that facilitate rotation of the hand piece relative to the housing/main chamber section 29, and not to affect significantly the rotational accuracy, a contact including compliant or resilient metal, and/or a coated polymer can be disposed between the rotatable, electrically conductive members 29, 30. This can ensure a negligible resistance (e.g., less than 0.01 ohm) between the hand piece 30 casing and the housing/main chamber 29, such that adequate, safe grounding is provided to the hand piece 30, without substantially sacrificing accurate, user-controlled rotatability of the hand piece-housing arrangement. Such a contact to ground the hand piece may be provided regardless of whether it contains any powered devices and/or components thereof.

Adequate safe grounding is typically described as the application of 25 Amps current across the entire system, if a limit of no more than 0.1 ohm resistance for equipment with a fixed power cord and no more than 0.2 ohms resistance for equipment with a detachable power cord is maintained. In order to maintain the overall resistance below such a specified threshold (e.g., 0.2 ohm, 0.1 ohm, 0.05 ohm, etc.), the materials and structure of the contact are selected such that the individual contact resistance is less than about 10 milliohms.

In one embodiment, clear aperture sections 24, 26 are made from an insulator material, such as carbon fiber, to ensure that all instrumentation located therein are electrically isolated or floating relative to the hand piece 30. To this end, the insulator material is selected to provide electrical isolation at a voltage of at least 1000 V, 1500 V, 2000 V, 5000 V, 10 KV, 20 KV, etc. In this embodiment, a single grounding wire that provides grounding to various sections is not needed. If a low resistance (e.g., less than 0.01 ohm, 0.05 ohm, 0.1 ohm, etc.) contact is provided between the hand piece 30 and the housing/main chamber 29, as described above, it is generally safe to use the hand piece 30 in a person's mouth. In this embodiment, as the grounding of the housing/main chamber 29 and hand piece 30, together is not affected by the grounding of the other sections of the system 100, resistance of the contact between the housing/main chamber 29 and hand piece 30 can be grater, though less than the specified threshold, than the permitted value of the contact resistance when instruments in the other sections (e.g., apertures 24, 26) are not isolated from or floating relative to the instruments in the housing/main chamber 29 and the hand piece 30. By using a relatively high resistance contact, rotatability of the hand piece 30 can be improved.

In some embodiments, an outer layer of the hand piece is made from an insulating material. In these embodiments, the hand piece may be floated, i.e., it may include two separate layers of insulation separating the outer, exposed surface of the hand piece from any powered instruments and/or powered components thereof that are disposed within the hand piece. In addition, instead of grounding, the handpiece may be attached to the housing/main chamber via an insulator contact that can withstand a specified voltage potential difference, e.g., at a voltage potential difference of at least about 500 V, 1 KV, 1.5 KV, 2 KV, 5 KV, 10 KV, 20 KV, etc.

Figure 2:
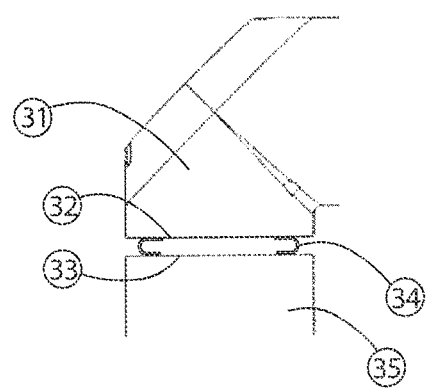
FIG. 2 is a schematic representation of a cross-sectional view of a mechanical-optical swivel joint with grounding fingers to provide reliable electrical conduction across the joint in accordance with one embodiment of the invention.

With reference to FIG. 2, a rotating optical knuckle 31 is coupled to a conduit 35, so that the two sections can rotate freely relative to each other while a laser beam may pass through the axis of the rotation. The rotating knuckle 31 having insulating material and the conduit 35 also containing insulating material can electrically isolate the section 31 from section 35. To this end, the insulator material is selected to provide electrical isolation at a voltage of at least 1000 V, 1500 V, 2000 V, 5000 V, 5 KV, 10 KV, 20 KV, etc.

Alternatively, the knuckle 31 and the conduit 35 can be electrically grounded to each other via flexible (e.g., resilient and compliant) electrically conductive fingers 34 compressed between the respective rims 32, 33 of the sections 31, 35. By disposing one or more flexible conductive fingers 34 in some or all rotating joints in a laser beam delivery section, a laser beam delivery system can be grounded to meets the grounding requirements specified above, without needing a grounding cable running along various section of the beam-delivery system.

Having described herein illustrative embodiments of the present invention, persons of ordinary skill in the art will appreciate various other features and advantages of the invention apart from those specifically described above. It should therefore be understood that the foregoing is only illustrative of the principles of the invention, and that various modifications and additions can be made by those skilled in the art without departing from the spirit and scope of the invention. Accordingly, the appended claims shall not be limited by the particular features that have been shown and described, but shall be construed also to cover any obvious modifications and equivalents thereof.

What is claimed is:

1. An electrically safe treatment system for use in treating a patient, the treatment system comprising:
    a first section comprising a first electrical component;
    a second section rotatably affixed to the first section; and
    a third section comprising a second electrical component and rotatably affixed to the first section via an insulator joint adapted to provide electrical isolation between the first electrical component and the second electrical component at least at a potential voltage at a specified value,
    wherein at least one of the first and second electrical components is selected from the group consisting of a servo motor, an intra-oral camera, a caries fluorescence sensor, a two-dimensional measurement scanner, and a three-dimensional measurement scanner.

2. The system of claim 1, wherein the third section further comprises a substantially electrically non-conductive material.

3. The system of claim 2, wherein the substantially electrically non-conductive material comprises carbon fiber.

4. The system of claim 1, wherein the insulator joint comprises a knuckle joint.

5. An electrically safe treatment system for use in treating a patient, the treatment system comprising:
    a first section comprising a first electrical component;
    a second section rotatably affixed to the first section; and
    a third section comprising a second electrical component and rotatably affixed to the first section via an insulator joint adapted to provide electrical isolation between the first electrical component and the second electrical component at least at a potential voltage at a specified value of at least about 2000 volts.

6. The system of claim 5, wherein the third section further comprises a substantially electrically non-conductive material.

7. The system of claim 5, wherein the insulator joint comprises a knuckle joint.

8. The system of claim 5, wherein the third section further comprises a laser generator comprising a radio-frequency (RF) excited $CO_2$ laser filled with gas at a pressure in a range of about 260 to 600 Torr.

9. An electrically safe treatment system for use in treating a patient, the treatment system comprising:
    a first section comprising a first electrical component and a housing forming a chamber of a laser beam delivery system;
    a second section rotatably affixed to the first section and comprising a hand piece adapted to guide a laser beam to a treatment area; and
    a third section comprising an articulating arm and a second electrical component comprising a laser generator, the third section rotatably affixed to the first section via an insulator joint.

10. The system of claim 9, wherein the laser generator comprises a radio-frequency (RF) excited $CO_2$ laser filled with gas at a pressure in a range of about 260 to 600 Torr.

11. The system of claim 9, wherein the third section further comprises a substantially electrically non-conductive material.

12. The system of claim 9, wherein the insulator joint comprises a knuckle joint.

13. A method of maintaining an electrically safe treatment system for use in treating a patient, the method comprising:
    providing a treatment system comprising:
        a first section comprising a first electrical component;
        a second section rotatably affixed to the first section; and
        a third section comprising a second electrical component and rotatably affixed to the first section; and
    providing an insulator joint between the first section and the third section, the insulator joint adapted to provide electrical isolation between the first electrical component and the second electrical component at least at a potential voltage at a specified value,
    wherein at least one of the first and second electrical components is selected from the group consisting of a servo motor, an intra-oral camera, a caries fluorescence sensor, a two-dimensional measurement scanner, and a three-dimensional measurement scanner.

14. The method of claim 13, wherein the third section further comprises a substantially electrically non-conductive material.

15. The method of claim 13, wherein the insulator joint comprises a knuckle joint.

16. The method of claim 13, wherein the third section further comprises a laser generator comprising a radio-frequency (RF) excited $CO_2$ laser filled with gas at a pressure in a range of about 260 to 600 Torr.

17. A method of maintaining an electrically safe treatment system for use in treating a patient, the method comprising:
    providing a treatment system comprising:
        a first section comprising a first electrical component;
        a second section rotatably affixed to the first section; and
        a third section comprising a second electrical component and rotatably affixed to the first section; and
    providing an insulator joint between the first section and the third section, the insulator joint adapted to provide electrical isolation between the first electrical component and the second electrical component at least at a potential voltage at a specified value of at least about 2000 volts.

18. The method of claim 17, wherein the third section further comprises a substantially electrically non-conductive material.

19. The method of claim 17, wherein the insulator joint comprises a knuckle joint.

20. The method of claim 17, wherein the third section comprises a laser generator comprising a radio-frequency (RF) excited $CO_2$ laser filled with gas at a pressure in a range of about 260 to 600 Torr.

21. A method of maintaining an electrically safe treatment system for use in treating a patient, the method comprising:
    providing a treatment system comprising:
        a first section comprising a first electrical component and a housing forming a chamber of a laser beam delivery system;

a second section rotatably affixed to the first section and comprising a hand piece adapted to guide a laser beam to a treatment area; and a third section comprising an articulating arm and a second electrical component comprising a laser generator and rotatably affixed to the first section via an insulator joint.

22. The method of claim 21, wherein the laser generator comprises a radio-frequency (RF) excited $CO_2$ laser filled with gas at a pressure in a range of about 260 to 600 Torr.

* * * * *